United States Patent
Hsiao et al.

(10) Patent No.: US 6,262,335 B1
(45) Date of Patent: *Jul. 17, 2001

(54) TRANSGENIC MICE EXPRESSING APP MUTANT AT AMINO ACIDS 717, 721 AND 722

(75) Inventors: Karen Hsiao, North Oaks, MN (US); David R. Borchelt; Sangram S. Sisodia, both of Baltimore, MD (US)

(73) Assignees: Johns Hopkins University, Baltimore, MD (US); Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/019,973

(22) Filed: Feb. 6, 1998

Related U.S. Application Data (63) Continuation of application No. 08/189,064, filed on Jan. 27, 1994, now abandoned.

(51) Int. Cl.[7] .................. A01K 67/00; A01K 67/027; G01N 33/00; C12N 15/00

(52) U.S. Cl. .................. 800/12; 800/3; 800/18; 800/25

(58) Field of Search .................. 800/3, 8, 12, 13, 800/14, 18, 25; 435/320.1

(56) References Cited

U.S. PATENT DOCUMENTS

| | | | |
|---|---|---|---|
| 4,873,191 | 10/1989 | Wagner et al. | 435/172.3 |
| 5,387,742 | 2/1995 | Cordell | 800/2 |
| 5,455,169 | 10/1995 | Mullan | 435/240.02 |
| 5,604,102 | 2/1997 | McConlogue et al. | 435/7.1 |
| 5,612,486 | 3/1997 | McConlogue et al. | 800/2 |
| 5,877,399 | * 3/1999 | Hsiao et al. | 800/2 |

FOREIGN PATENT DOCUMENTS

| | | |
|---|---|---|
| 0 451 700 A1 | 10/1991 | (EP) . |
| 0653 154 A2 | 5/1995 | (EP) . |
| WO 89/06689 | 7/1989 | (WO) . |
| WO 91/19810 | 12/1991 | (WO) . |
| WO 92/06187 | 4/1992 | (WO) . |
| WO 9213069A | 8/1992 | (WO) . |
| WO 930189A1 | 2/1993 | (WO) . |
| WO 93/14200 | 7/1993 | (WO) . |
| WO95/11968 | 5/1995 | (WO) . |

OTHER PUBLICATIONS

Lannfelt et al., "Alzheimer's disease: molecular genetics and transgenic animals models", *Behavioural Brain Research*, 57 (1993), pp. 207–213.
Felsenstein et al., Alz. and Parkin. Diseases, ed., I. Hanin et al., Plenum Press, New York, NY, pp. 401–409 (1995).
Moran et al. "Age–related learning deficits in transgenic mice expressing the 751–amino acid isoform of human β–amyloid precursor protein", *Proc. Natl. Acad. Sci. USA*, vol. 92, Jun. 1995, pp. 5341–5345.
Higgins et al., (1993), Annals N.Y. Acad. Sci. 695, 224–227.
Chartier–Harlin et al., *Nature*, (1991) 353: 844–846.
Fukuchi et al., *Society for Neuroscience Abstracts*, (1993) 19:1035.
Goate et al., *Nature* (1991) 349:704–706.
Goldgaber et al. *Science* (1987) 235: 877–880.
Greenberg, *Society for Neuroscience Abstracts* (1993) 19:1035.
Hendriks et al., *Nature Genetics* (1992) 1:218–221.
Hsiao et al., *Science* (1990) 250:1587–1590.
Kammescheidt et al., *Proc. Natl. Acad. Sci. USA* (1992) 89:10857–10861.
Kang et al., *Nature* (1987) 325:733–736.
Kawabata et al., *Nature* (1991) 354:476–478.
Kitaguchi et al., *Nature* (1988) 331:530–532.
Kozak, *J. Cell Biology* (1989) 108:229–241.
Lamb et al., *Nature Genetics* (1993) 5: 22–30.
Levy et al., *Science* (1990) 248: 1124–1126.
Lieberburg, Abstract 421.15 *Society for Neuroscience Abstracts* (1993) 19:1035.
Mullan et al., *Nature Genetics* (1992) 1:345–347.
Murrell et al., *Science* (1991) 254: 97–99.
Ponte et al., *Nature* (1988) 331: 525–527.
Quon et al., *Nature*, (1991) 352: 239–241.
Robakis et al., *Proc. Natl. Acad. Sci., USA* (1987) 84: 4190–4194.
Savage et al., *Society for Neuroscience Abstracts* (1993) 19:1035.
Howland et al., *Society for Neuroscience Abstracts* (1993) 19:1035.
Scott et al., *Cell* (1989) 59:847–857.
Tanzi et al., *Science* (1987) 235:880–884.
Tanzi et al., *Nature* (1988) 331:528–530.
Wirak et al., *Science* (1991) 253:323–325.
Scott et al., *Protein Science* (1992) 1:986–997.
Wirak et al., *EMBO J* (1991) 10:289–296.
Hyman et al., *Current Opinion Neurol. Neurosurg.* (1992) 5:88–93.
Sandu et al., *J. Biol. Chem.* (1991) 266:21331–21334.
Lannfelt et al (1993) Behav. Brain Res. 207–213.*
Felsenstein et al (1995) Alz. Parkinson's Diseases, ed. I. Hannin et al, Plenum Press, New York, Ny 401–409.*
Higgins et al (1993) Annals NY Acad. Sci. 695, 224–227.*
Scott et al (1989) Cell 59, 847–857.*
Mullen et al (1992) Nature Genetics 1, 345–347.*
Quon et al (1991) Nature 352, 239–241.*
Lannfelt et al (1993) Behav. Brain Res. 57, 207–213.*
Hggins et al (1993) Annals NY Acad, Sci. 695, 224–227.*
Moran et al (1995) Proced. Natl. Acad. Sci. 92, 5341–5345.*

* cited by examiner

*Primary Examiner*—Deborah Crouch
(74) *Attorney, Agent, or Firm*—Fish & Richardson P.C.

(57) ABSTRACT

A transgenic non-human eukaryotic animal whose germ cells and somatic cells contain the amyloid precursor protein sequence introduced into the animal, or an ancestor of the animal, at an embryonic stage.

13 Claims, 5 Drawing Sheets

1. KM670/671NL
2. A692G
3. E693Q
4. V717I
5. V717G
6. V717F
7. VVM717/721/722IAV

Fig.3

■ 1.6 kb 3'-untranslated sequence

Fig.4

■ APP coding sequence with CS1 translation initiation sequence as illustrated in FIG. 6

Fig.5

■ APP coding sequence with CS2 translation initiation sequence as illustrated in FIG. 7

A = CTG ACC ACT CGA CCA GGT TCT GGG T
P = GTG GAT AAC CCC TCC CCC AGC CTA GAC CA

■ APP CODING SEQUENCE

▦ 1.6 kb SEQUENCE FROM HAMSTER PrP 3'-UNTRANSLATED REGION

— DNA SEQUENCES FROM THE HAMSTER PrP COSMID VECTOR AS ILLUSTRATED IN FIGS. 4&5

SEQUENCE LISTING

```
<160> NUMBER OF SEQ ID NOS:  16

<210> SEQ ID NO 1
<211> LENGTH: 9
<212> TYPE: DNA
<213> ORGANISM: Homo Sapiens

<400> SEQUENCE: 1 gcgatgctg                                                            9

<210> SEQ ID NO 2
<211> LENGTH: 9
<212> TYPE: DNA
<213> ORGANISM: Artificial Sequence:
<220> FEATURE:
<223> OTHER INFORMATION: Description of Artficial Sequence: Translation
      initiation sequence

<400> SEQUENCE: 2 accatgctg                                                            9

<210> SEQ ID NO 3
<211> LENGTH: 9
<212> TYPE: DNA
<213> ORGANISM: Atificial Sequence:
<220> FEATURE:
<223> OTHER INFORMATION: Description of Artficial Sequence: Translation
      initiation sequence

<400> SEQUENCE: 3 accatggtg                                                            9

<210> SEQ ID NO 4
<211> LENGTH: 9
<212> TYPE: DNA
<213> ORGANISM: Mus musculus

<400> SEQUENCE: 4 acgatgctg                                                            9
```

<210> SEQ ID NO 5
<211> LENGTH: 9
<212> TYPE: DNA
<213> ORGANISM: Mus musculus

<400> SEQUENCE: 5 atcatggcg                                                                    9

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 6
aagtcgacac catgctgccc ggtttggcac t                                           31

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
aaggtacctc ccagcgcccg agcc                                                   24

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
aaaaaagtcg acaccatggt gcccggtttg gcact                                       35

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 9
aaggtacctc cagcgcccga gcc                                                    23

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 10
ccgagatctc tgaagtgaag atggatg                                                27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

```
-continued

<400> SEQUENCE: 11
aagcttggcg cctttgtttg aacccac                                              27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 12
ccgagatctc tgaagtgaat ctggatgc                                             28

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence: Translation
      initiation sequence

<400> SEQUENCE: 13
gtcgacacca tgc                                                             13

<210> SEQ ID NO 14
<211> LENGTH: 13
<212> TYPE: DNA
<213> ORGANISM: Artificial Sequence
<220> FEATURE:
<223> OTHER INFORMATION: Description of Artificial Sequence: Translation
      initiation sequence

<400> SEQUENCE: 14
gtcgacacca tgg                                                             13

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 15
ctgaccactc gaccaggttc tgggt                                                25

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 16
gtggataacc cctcccccag cctagacca                                            29
```

TRANSGENIC MICE EXPRESSING APP MUTANT AT AMINO ACIDS 717, 721 AND 722

This is a continuation of U.S. application Ser. No. 08/189,064, filed Jan. 27, 1994, abandoned.

NOTICE REGARDING FEDERAL FUNDING

This research was supported in part by grants from the National Institutes of Health, including grant number K08-NA01419. The government may have rights in this invention.

TECHNICAL FIELD

The invention relates to transgenic animals with a progressive neurologic disease resembling Alzheimer's disease.

BACKGROUND

Alzheimer's disease (AD) is a progressive, fatal neurodegenerative disorder of the elderly. AD shows a slowly progressive mental deterioration with failure of memory, disorientation and confusion leading to profound dementia. There are several histologic features, but two are striking. First, argyrophilic plaques comprised of the amyloidogenic Aβ fragment of amyloid precursor protein (APP) are scattered throughout the cerebral cortex and hippocampus. Second, neurofibrillary tangles are found in pyramidal neurons predominantly located in the neocortex, hippocampus, and nucleus basalis of Meynert. There are other changes, also. Granulo-vacuolar degeneration in the pyramidal cells of the hippocampus has been considered by some to be more specific for AD than plaques or neurofibrillary tangles. Finally, there is neuronal loss and gliosis in the cerebral cortex and hippocampus.

There are patients with dementia who lack the pathologic features of AD (and by definition have a different disease), and conversely, there are individuals with many of the pathologic features of AD who were not demented prior to death. The diagnosis of AD requires that both the clinical and the pathological features characteristic for the disease be present in the patient; the diagnosis cannot be made with certainty from either clinical or pathological features alone. Whether neural dysfunction and clinical abnormalities precede the development of these pathologic features, particularly the amyloid plaques and neurofibrillary tangles, is unknown.

The clinical manifestations of AD predict the regions of affected brain structures in the forebrain, including the cerebral cortex, hippocampus, amygdala, and parahippocampal gyri. These regions are known as the cortico-limbic areas of the brain. The basal ganglia is spared, as is the hindbrain, including the cerebellum, the pontine and the medullary nuclei. Within the cerebral neocortex, the primary cortical areas area relatively spared, which corresponds to the relative clinical sparing of basic motor and sensory cortical functions.

Transgenic mice harboring APP transgenes have been described; however, transgene product expression falls considerably short of endogenous levels of APP (total APP levels in the other transgenic mice have not exceeded 150% of endogenous levels), and fails to generate a disease phenotype with a progressive neurobehavioral disorder accompanied by pathology in the cortico-limbic regions of the brain. In these other transgenic mice, there have been no signs of a progressive neurologic disorder or of neuropathologic changes in the brain which may be regarded as evidence of a true neurologic disease.

Preamyloid APP plaques have been observed in some transgenic mice. However, preamyloid APP plaques are not necessarily indicative of a disease, since they are routinely observed in human brain regions, such as the cerebellum, which are devoid of other signs of pathology or clinical manifestations. Increased APP immunoreactivity located within vesicular structures in hippocampal neurons of transgenic mice has been reported, but the significance of this immunoreactivity is unclear since the mice exhibited neither a progressive neurobehavioral disorder nor evidence of true neuropathology.

It therefore is of interest to develop a transgenic nonhuman mammalian model for AD wherein the animal develops a progressive neurologic disease of the cortico-limbic brain resembling AD, both clinically and pathologically (e.g. the gliosis and the specific brain regions affected). It also is desirable that the animal develops neurologic disease within a fairly short period of time from birth, facilitating the analysis of multigenerational pedigrees. The model can be used to study the pathogenesis and treatment of AD since there is a distinct and robust clinical and pathologic phenotype to examine and score.

Relevant Literature

Quon et al. (1991) *Nature* 352:239 describe transgenic mice containing human amyloid precursor protein genes. Lamb et al. (1993) *Nature Genetics* 5:22 describe transgenic mice in which the amount of amyloid precursor protein expressed is approximately 50% over endogenous levels.

Other transgenic mouse studies of Alzheimer amyloid precursor (APP) protein include the following. Greenberg, B. D. (1993) Abstract 421.12, *Society for Neuroscience Abstracts* 19:1035. The APP protein gene was expressed using mAPP and mMt-I promoters. Schwartz, D. A. et al. (1993) disclose neuron-specific expression of human beta-amyloid precursor protein (APP) in transgenic mice. Abstract 421.13, *Society for Neuroscience Abstracts* 19:1035. Savage, F. A. et al. (1993) disclose human amyloid precursor protein expression in transgenic mice as a model of Alzheimer's disease: search for pathology. Abstract 421.14, *Society for Neuroscience Abstracts* 19:1035. Lieberburg, I. (1993) disclose expression of human protein in transgenic mice using the NSE promotor. Abstract 421.15, *Society for Neuroscience Abstracts* 19:1035. Fukuchi, K. et al. (1993) disclose intestinal beta-amyloidosis in transgenic mice. Abstract 421.16, Society for *Neuroscience Abstracts* 19:1035. A chicken beta-actin promotor and CMV enhancer were used for expressing the APP protein gene.

Wagner et al. (1981) *P.N.A.S. U.S.A.* 78:5016 describe transgenic mice containing human globin genes. Scott et al. (1989) *Cell* 59:847 describe transgenic mice containing hamster prion protein genes. Hsiao et al. (1990) *Science* 250:1587 describe transgenic mice containing mutant human prion protein genes. Hsiao disclosed a model for Gerstmann-Straussler-Scheinker disease (GSS), a rate neurodegenerative disease caused by mutations in the prion protein (PrP) gene, in transgenic mice in which levels of mutant transgene product exceeding endogenous levels were needed to generate a clinical and pathological phenotype (Hsiao et al., 1991; Hsiao, et al., 1993).

SUMMARY OF THE INVENTION

A transgenic non-human animal model for Alzheimer's disease is provided, together with methods and compositions for preparation of the animal model and methods for using it. The non-human mammals are obtained by the steps of introducing multiple copies of an expression cassette into the non-human mammal at an embryonic stage, and developing the embryo to term in a pseudo-pregnant foster female. The expression cassette comprises an amyloid precursor protein coding sequence operably joined to regulatory sequences for expression of the coding sequence in neurologic tissues at a level at least two to four-fold that of endogenous levels of wild-type amyloid precursor protein. The resulting transgenic non-human mammals develop progressive neurologic disease in the cortico-limbic areas of the brain. The transgenic animals find use for example in screening protocols for treatment and prevention of Alzheimer's disease.

DESCRIPTION OF THE PREFERRED EMBODIMENTS

The invention is directed to a transgenic non-human eukaryotic animal, preferably a rodent, such as a mouse, together with methods and compositions for preparing and using the animal. The animal expresses an amyloid precursor protein (APP) sequence at a level in brain tissues such that the animal develops a progressive neurologic disorder within a short period of time from birth, generally within a year from birth, preferably within 2 to 6 months, from birth. The APP protein sequence is introduced into the animal, or an ancestor of the animal, at an embryonic stage, preferably the one-cell, or fertilized oocyte, stage, and generally not later than about the 8-cell stage. The zygote or embryo is then developed to term in a pseudo-pregnant foster female. The amyloid precursor protein genes are introduced into an animal embryo so as to be chromosomally incorporated in a state which results in the supra-endogenous expression of the amyloid precursor protein and the development of a progressive neurologic disease in the cortico-limbic areas of the brain, areas of the brain which are prominently affected in AD.

AD research has been seriously impeded by the lack of easily accessible animal models. Some aspects of the neuropathology of aged primates are similar to human AD (Price et al., 1992). Aged primates develop β-amyloid plaques and forme fruste neurofibrillary tangles. No other animals studied develop disease resembling AD as closely as aged primates. However, aged primates are impractical to study in large numbers; their use raises both moral and economic issues. Applicants are unaware of other animal models of AD which exhibit appropriate clinical and pathological phenotypes.

Missense point mutations in the gene coding for the amyloid precursor proteins have been linked to familial AD. However, despite the discovery of disease-associated mutations in APP, all published attempts to create transgenic animals with AD have involved only wild-type APP transgenes in mice (Kawabata et al., 1991; Quon et al., 1991; Wirak et al., 1991; Kammesheidt et al., 1992; Lamb et al., 1993). Unfortunately, several of the published studies purporting pathology have been confounded by inadequate documentation of transgene product expression and/or misinterpretation of pathology. Two have been retracted (Kawabata, et al., 1991; Wirak, et al., 1991). Previous efforts to create a model of AD in transgenic mice have been discouraging. In most cases, transgene product expression comparable to or exceeding endogenous levels of APP was not achieved, and in no case did transgenes encode mutated APP. In some cases, the entire APP gene was not expressed, just the carboxyl terminus (Kammesheidt, et al., 1992); this may overlook the biologic effects that the rest of the APP molecule may exert in AD.

The present invention offers several advantages over existing models. The transgenic animals express mutant APP and develop a neurologic illness accompanied by premature death. Gliosis and intracellular APP/Aβ accretions are present in the hippocampus and cerebral cortex. The gliosis and clinical manifestations in affected transqenic animals are indicative of a true neurologic disease. The progressive neurologic disease is characterized by diminished exploratory/locomotor behavior and diminished 2-deoxyglucose uptake/utilization and hypertrophic gliosis in the cortico-limbic regions of the brain. No other Alzheimer models develop a progressive neurobehavioral disorder, gliosis and diminished 2-deoxyglucose uptake/utilization in the cortico-limbic regions of the brain, or any other region of the brain.

The expression cassette will include in the 5'-3' direction of transcription, a transcriptional and translational initiation region associated with gene expression in brain tissue, DNA encoding an APP, and a transcriptional and translational termination region functional in the host animal. One or more introns may also be present. Of particular interest are initiation regions (also sometimes referred to as "promoters") which provide for preferential or at least substantially specific expression in brain as compared to other tissue. By "at least substantially" is intended that expression in brain tissue is greater than about 100 fold that in other tissue. Within the brain, of particular interest is expression in the cortico-limbic area. The transcriptional initiation region may be endogenous to the host animal or foreign or exogenous to the host animal. By foreign is intended that the transcriptional initiation region is not found in the wild-type animal host into which the transcriptional initiation region is introduced. By endogenous, is intended sequences indigenous (i.e. natural to) the host animal as well as those present in the host animal as a result of an infectious disease, e.g. viral, prion, and the like.

The promoter preferably comprises a transcriptional initiation regulatory region and translational initiation regulatory region of untranslated 5' sequences, "ribosome binding sites," responsible for binding mRNA to ribosomes and translational initiation. The transcriptional initiation regulatory region may be composed of cis-acting subdomains which activate or repress transcription in response to binding of trans acting factors present in varying amounts in different cells. It is preferred that all of the transcriptional and translational functional elements of the initiation control region are derived from or obtainable from the same gene. In some embodiments, the promoter will be modified by the addition of sequences, such as enhancers, or deletions of non-essential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

Of particular interest as a transcriptional initiation region is one from a prion protein gene which is functional in the brain of the host animal. Prion protein is implicated in the pathogenesis and transmission of Gerstmann-Straussler syndrome and in scrapie, an equivalent animal disease. Brain tissue from infected animals serves as a source for nucleic acid for preparing the desired sequences. To identify a prion promoter having the desired characteristics, where a prion protein has been or is isolated, it may be partially sequenced, so that a probe may be designed for identifying mRNA specific for prion protein. To further enhance the concentration of the mMNA specifically associated with prion protein, cDNA may be prepared and the cDNA subtracted with messenger RNA or cDNA from non-infected brain tissue. The residual cDNA may then be used for probing the genome for complementary sequences, using an appropriate library prepared from brain tissue from infected animals. Sequences which hybridize to the CDNA may then be isolated, manipulated, and the 5'-untranslated region associated with the coding region isolated and used in expression constructs to identify the transcriptional activity of the 5'-untranslated region. As appropriate, sequences can be amplified using PCR procedures known to those skilled in the art. In some instances, a probe may be employed directly for screening a genomic library and identifying sequences which hybridize to the probe. The sequences will be manipulated as described above to identify the 5'-untranslated region.

Tissue-specific transcription suggests that gene regulatory proteins may be bound to enhancer sequences and other upstream promoter elements. By enhancer element ("enhancer") is intended a regulatory DNA sequence that is capable of activating transcription from a promoter linked to it with synthesis beginning at the normal RNA start site; which is capable of operating in both orientations (normal or flipped); and which is capable of functioning even when moved either upstream or downstream from the promoter. Both enhancers and other upstream promoter elements bind sequence specific DNA-binding proteins that mediate their effects.

To identify the exact nucleotide sequences important for the function of the enhancers(s), and other upstream elements, fragments of the prion protein untranslated 5'-region are screened for their capacity to bind nuclear proteins and for their ability to function with a heterologous promoter. Binding experiments with nuclear proteins from brain tissue can be used to determine the presence of enhancer and silencer sequences; the protein binding studies can be used to pinpoint specific nucleotide sequences that bind to a corresponding series of gene regulatory proteins.

The activity of each enhancer and other upstream promoter elements generally is present on a segment of DNA which may contain binding sites for multiple proteins. The binding sites can generally be dissected by preparing smaller mutated versions of the enhancer sequence joined to a reporter gene whose product is easily measured. The effect of each mutation on transcription can then be tested. Alternatively, fragments of this region can be prepared. Each of the mutated versions of the enhancer sequence or the fragments can be introduced into an appropriate host cell and the efficiency of expression of the reporter gene measured. Those nucleotides required for enhancer function in this test are then identified as binding sites for specific proteins by means of gel mobility shift and DNA foot printing studies.

An alternate means of examining the capability of isolated fragments of the region upstream of the promoter to enhance expression of the reporter gene is to look for sub-domains of the upstream region that are able to enhance expression levels from a test promoter which comprises the TATA CAAT box but shows little or no detectable activity. A fragment of the 5'-region is inserted in front of the test promoter in an expression cassette, and the effect on expression of the reporter gene evaluated.

Of particular interest for brain-specific expression copy number dependent expression are regions capable of binding to nuclear proteins in the region up to about 20 kb from the mRNA start site of the prion protein gene. Within this region, there may be several subdomains of interest having the characteristics of brain specific enhancer elements which can be evaluated by using constructs.

A promoter from a gene expressed in brain tissue of the host animal may be employed for varying the phenotype of the host animal. The transcriptional level should be sufficient to provide an amount of RNA capable of resulting in a modified animal. By "modified animal" within the subject invention is meant an animal having a detectably different phenotype from a non-transformed animal of the same species, for example one not having the transcriptional cassette including APP coding sequences in its genome. Various changes in phenotype are of interest. These changes may include progressive neurologic disease in the cortico-limbic areas of the brain expressed within a short period of the time from birth; increased levels of expression of an APP gene above endogenous expression and the development of a neurologic illness accompanied by premature death; gliosis and intracellular APP/A$\beta$ accretions present in the hippocampus and cerebral cortex; progressive neurologic disease characterized by diminished exploratory/locomotor behavior and diminished 2-deoxyglucose uptake/utilization and hypertrophic gliosis in the cortico-limbic regions of the brain.

The termination region which is employed primarily will be one of convenience, since the termination regions appear to be relatively interchangeable. The termination region may be native with the transcriptional initiation region, may be native with the DNA sequence of interest, or may be derived from another source. Convenient termination regions are available from the prion protein gene.

The expression cassette which is used in the subject invention includes promoter and enhancer sequences from a gene which is expressed in the brain and preferably which is expressed in a manner that is related to the number of such sequences incorporated into the chromosome, namely that higher transcription occurs with a larger number of transgene copies incorporated into the chromosome, operably joined to an APP gene sequence and translational and transcriptional termination regions. Examples of promoter and enhancer sequences which are expressed in brain and which drive copy number dependant expression include the prion protein promoter, such as that described by Scott et al. *Protein Science* (1992) 1:986–987, together with sequences upstream from the promoter, because in order to obtain copy number dependant expression, it generally is necessary to include a sufficiently large region of DNA controlling transcription so that it is large enough to be relatively unaffected by position effects. As an example, for the prion protein gene from hamster, approximately 20kb of sequence upstream of the promoter can be used.

Construction of a cosmid vector for use in the instant invention includes assembling in the 5' to 3' direction promoter and enhancer sequences of the prion protein gene, the coding region of an APP gene sequence of interest and transcriptional and translational termination sequences operably attached to a cosmid vector for delivery of the DNA constructs into the pronuclei of mouse eggs for expression of an APP gene in brain tissue. The enhancer sequences may include a 20 kb region upstream of the prion protein promoter and may also include the noncoding exon 1 and the 10 kb intron downstream of exon 1 from the prion protein gene. The promoter containing the transcriptional and translational initiation regions may contain nucleotides A and G at positions −3 and +4, respectively, relative to the initiation codon for optimal translation. Using molecular genetic techniques well known in the art, the promoter/enhancer region of the prion protein gene may be isolated from a mammalian genomic cosmid clone used to create transgenic mice which express prion protein. The coding sequence of an APP gene is inserted between the promoter/enhancer region and the termination sequences at a unique restriction site-or sites such that the coding sequence is translated in-frame. An APP protein in transgenic brain tissue introduced using a cosmid vector as described above may be confirmed to be at least two to four-fold that of endogenous levels.

A major obstacle to the creation of a transgenic model of AD has been the inability to overexpress transgenic APP protein in the brain of the transgenic animal. In some cases, mRNA is well expressed, but the protein is poorly expressed. This indicates that the strength of promoters used may be adequate, but that protein translation may not be optimal. Poor translation may result from a weak translation initiation sequence. Accordingly, it may be necessary to include a translation initiation sequence wherein the positions at minus three and plus four relative to the initiation codon are A and G, respectively. See Table 1 below.

TABLE 1

Transgene Translation Initiation Sequence Optimization

| Transgene | Translation Initiation Sequence −3 +4 | |
|---|---|---|
| Hacos. CS0HuAPP695-V717Imyc | GCGATGCTG (native human APP) | SEQ ID NO:1 |
| Hacos.CS1 | ACCATGCTG | SEQ ID NO:2 |
| Hacos. CS2 | ACCATGGTG | SEQ ID NO:3 |
| Hacos.MoAPP695-WT | ACGATGCTG (native mouse APP) | SEQ ID NO:4 |
| Hacos.MoPrP-P101L | ATCATGGCG (native mouse PrP) | SEQ ID NO:5 |

Any amyloid precursor protein sequence can be used to produce the transgenic animals of the invention. An APP protein sequence, as the term is used herein, means a sequence of the coding region of the APP gene which, when incorporated into the genome of the animal in multiple copies and expressed in the transgenic animal at supra-endogenous levels, promotes a progressive neurologic disease in the transgenic animal. The neurologic disease is characterized by a neurobehavioral disorder with gliosis and diminished glucose uptake and/or utilization in cortico-limbic brain structures. The coding sequence can be from a wild-type gene, or from a gene containing one or more mutations. The coding sequence can be a natural sequence or a synthetic sequence or a combination of natural and synthetic sequences.

Human APP is encoded by a single 400-kb gene comprised of 18 exons on chromosome 21. Alternative mRNA splicing gives rise to three APP isoforms. Two forms, APP-751 and APP-770 contain a Kunitz-protease inhibitor (KPI) region; the third, APP-695, lacks the KPI segment. Preferred sequences are those which are disease-linked. Examples of disease-linked mutations include a mutation at APP codon 693 (of APP-770) linked to Dutch congophilic angiopathy (Levy et al., 1990), a mutation in APP linked to familial AD, valine→isoleucine at codon 717 (of APP-770) (Goate et al., 1991), a mutation wherein the valine at codon 717 is replaced by phenylalanine or glycine (Chartier-Harlin et al., 1991; Murrill et al., 1991); and in one family with both congophilic angiopathy and AD, a mutation wherein alanine is replaced by glycine at codon 692 (Hendriks et al., 1992). In a Swedish kindred, a double mutation at codons 670 and 671, resulting in a substitution of the normal lysine-methionine dipeptide by asparagine-leucine was found (Mullan et al., 1992).

Figure 6:
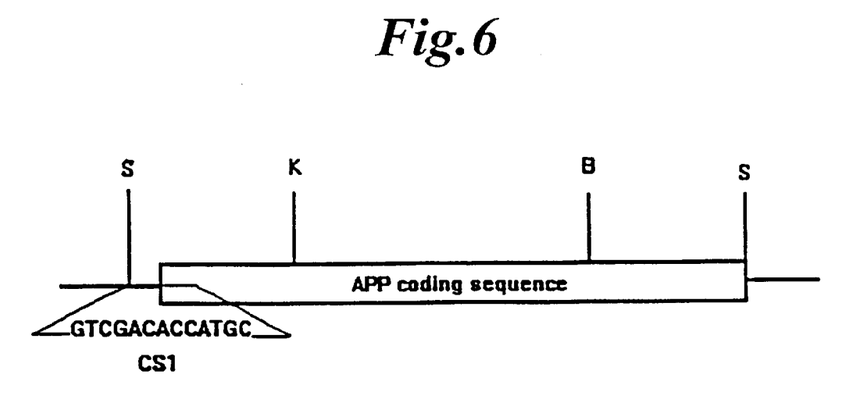
FIGS. 6 & 7 are diagrammatic representations of HUAPP sequences modified for strong translation initiation and flanking SalI restriction sites SEQ ID NOS:13 and 14.
Figure 7:
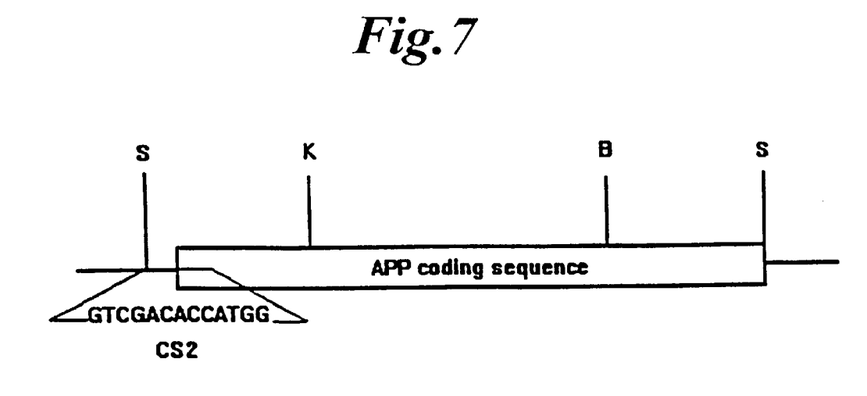

Table 2, below, lists some of the known amyloid precursor protein sequences, some of which are genetically linked to familial Alzheimer's disease. The abbreviations used in Table 2 refer to the following: CS1=translation initiation sequence as represented in FIG. 6; CS2=translation initiation sequence as represented in FIG. 7; V=valine;

I=isoleucine; G=glycine; F=phenylalanine; M=methionine; A=alanine; K=lysine; N=asponagine; L-leucine; E=glutamate; Q=glutamine; ORF=open reading frame; numeral in the 'Mutation' column refers to the mutated codon based upon the APP-770 numbering system.

TABLE 2

Examples of APP Transgenes

| Translation Initiation | APP ORF Species | ORF Size (codons) | Mutation |
|---|---|---|---|
| CS1 or CS2 | human, mouse or human/mouse chimeras | 695 & 751 or 770 | V717I V717G V717F VVM717/721/722IAV KM670/671NL770 A692G E693Q |

A transgenic organism is one that has an extra or exogenous fragment of DNA in its genome. In order to achieve stable inheritance of the exogenous DNA fragment, the integration event must occur in a cell type that can give rise to functional germ cells, either sperm or oocytes. Two animal cell types that can form germ cells and into which DNA can be readily introduced are fertilized egg cells and embryonic stem cells.

Of particular interest are novel chimeric APP genes, in which human Aβ sequences replace the Aβ region of mouse APP. A158,5 is a 4-kDa peptide derived from APP. Examination of human (Hu), mouse (Mo), and chimeric (Mo/Hu) APP processing in mouse cell lines indicates that tangible differences are evident. It appears that HuAPP matures poorly in mouse cells, relative to Mo- or Mo/HuAPP. However, the human Aβ sequences promote the formation of soluble Aβ peptides that are normally produced. Mo/HuAPP chimeric protein matures more efficiently than HUAPP, and generates more soluble Aβ than MoAPP.

Embryonic stem (ES) cells, can be returned from in vitro culture to a "host" embryo where they become incorporated into the developing animal and can give rise to cells of all tissues, including germ cells. The ES cells are transfected in culture and then the mutation is transmitted into the germline by injecting the cells into an embryo. The animals carrying mutated germ cells are then bred to produce transgenic offspring.

A preferred method for making the subject transgenic animals is by zygote injection. This method involves injecting DNA into a fertilized egg, or zygote, and then allowing the egg to develop in a pseudo-pregnant mother. The transgenic animal that is born is called a founder, and it is bred to produce more animals with the same DNA insertion. In this method of making transgenic animals, the new DNA typically randomly integrates into the genome by a nonhomologous recombination event. One to many thousands of copies of the DNA may integrate at one site in the genome. Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are then screened for the presence of the desired integrated DNA. By a pseudo-pregnant female is intended a female in estrous who has mated with a vasectomized male; she is competent to receive embryos but does not contain any fertilized eggs. Pseudo-pregnant females are important for making transgenic mice since they serve as the surrogate mothers for embryos that have been injected with DNA or embryonic stem cells. The host animal can be any animal, although generally the preferred host animal is one which lends itself to multigenerational studies. In some instances, however, a primate, for example a rhesus monkey may be desirable as the host animal, particularly for therapeutic testing.

Putative founders are screened for presence of the transgene in several ways. Brain APP protein and RNA expression are analyzed and the transgene copy number determined using methods known to those of skill in the art. The transgenic animals also are observed for clinical changes. Examples of neurobehavioral disorders for evaluation are poor mating response, diminished locomotor (exploratory behavior in a novel setting) and premature death. For transgene copy number, preferably the copy number is greater than five copies, more preferably greater than 30 copies, and most preferably greater than 60 copies. The amount of APP is that which produces a progressive neurologic disorder. Generally this amount is greater than two-fold that of endogenous APP, and most preferably greater than four-fold that of endogenous APP, although in some instances a lower amount of APP may be effective in producing a progressive neurologic disorder, particularly where the mutation in the APP occurs in the Aβ region, or just upstream of the Aβ region.

The founder animals can be used to produce stable lines of transgenic animals that express mutant APP. For ease of propagation, male founder mice are preferred. The animals are observed clinically. Analyses of transgene copy number (to exclude multiple transgene insertion sites), mRNA expression, protein expression, neuropathology, and glucose uptake in these animals are also performed. These studies provide information about the age of onset of illness, the duration of illness, the penetrance of the phenotype, the range of neuropathologic findings, regional brain dysfunction, and the dependence of phenotype upon levels of protein expression.

The animals also are screened using a species-appropriate neurobehavioral test. For example, for mice the "corner index" is used. This is a quick and simple neurobehavioral test to screen animals for evidence of brain pathology. Studies of locomotor/exploratory behavior in mice is a standard means of assessing the neuropsychology (File and Wardill, 1975; Loggi et al., 1991). Accordingly, a 'corner index' (CI), was established which measures the number of times a mouse puts its nose into the corners of a new clean cage during the first minute after it is place alone into that cage, since this sniffing is characteristic of exploration by a mouse. Based upon a number of observations with control mice, a provisional criterion for illness of three consecutive scores $\leq 4$ was established. The onset of illness is the first of the three consecutive testing dates in which scores $\geq 4$ are obtained. Animals are tested once or twice per week.

The validity of the CI is evaluated by conducting longitudinal measurements of the CI over time in non-transgenic male and female mice. The CI in transgenic mice which express mutant and wild-type APP is also measured. Initial data support the use of the CI because thus far a low CI ($\geq 4$) correlates with high mutant APP transgene copy numbers, premature death, and neuropathologic findings. The CI exhibits a dosage dependent relationship to transgene copy number, which supports the validity of its use in assessing neurobehavioral signs in transgenic mice. The neuropathology of the animals is also evaluated. Brain regions known to be affected by AD, such as those in the cortico-limbic region are particularly reviewed for changes including APP/Aβ excretions, gliosis, and changes in glucose uptake and utilization. Immunobiotic studies of various brain regions is used to detect transgene product.

The animals of the invention can be used as tester animals for materials, e. g. antioxidants such as Vitamin E or lazaroids, thought to confer protection against the development of AD. An animal is treated with the material, and a reduced incidence or delayed onset of neurologic disease, compared to untreated animals, is detected as an indication of protection. The animals can further be used as tester animals for materials thought to improve or cure Alzheimer's disease. An animal with neurologic disease is treated with the material, and a delayed death, or improvement in neurobehavior, gliosis, or glucose uptake/utilization, compared to untreated animals with neurologic disease, is detected as an indication of amelioration or cure.

The animals of the invention can be used to test a material or situation, e.g. oxidants or head trauma, suspected of accelerating or provoking Alzheimer's disease, by exposing the animal to the material or situation and determining neurobehavioral decline, premature death, gliosis, and diminished glucose uptake/utilization as indicators of its capacity to induce Alzheimer's disease. The method can further include testing therapeutic agents in animals exposed to a material or situation suspected of provoking Alzheimer's disease.

Careful characterization of the transgenic animals should lead to elucidation of the pathogenesis of AD. The sequence of molecular events in mutant APP metabolism leading to disease can be studied. The animals also are useful for studying various. proposed mechanisms of pathogenesis, including horizontal transmission of disease (Prusiner, 1987), oxidation and free-radical production (Blass and Gibson, 1991; Ames et al., 1993), inflammation (McGeer et al., 1993), Rogers et al., 1992) neurotrophic factor deprivation (Perry, 1990; Hefti and Schneider, 1991; Koliatsos et al., 1991), apolipoprotein E4 metabolism (strittmatter et al., 1993), and potassium channel dysfunction (Etcheberrigaray, et al., 1993). such knowledge would lead to better forms of treatment for this devastating illness. Kozak, et al. (1989) *J. Cell Biology* 108:299).

Other features and advantages of the invention will be apparent from the description of the preferred embodiments, and from the claims. The following examples are offered by way of illustration and not by way of limitation.

EXAMPLES

Example 1

PRP-APP FUSED GENES

Figure 1:
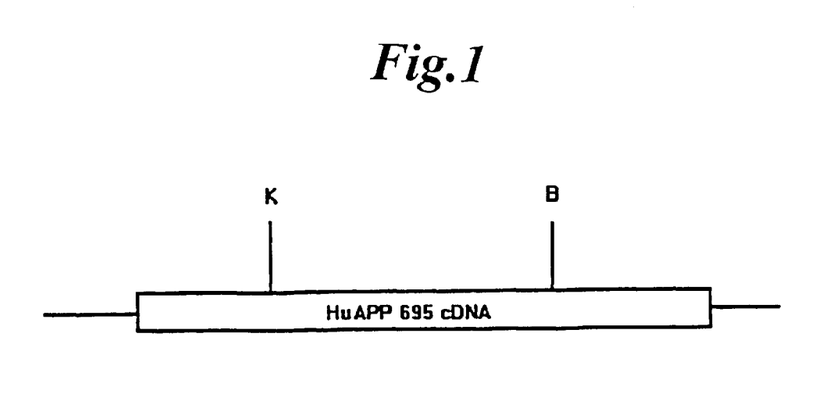
FIG. 1 is a diagrammatic representation of a HuAPP CDNA sequence.
Figure 2:
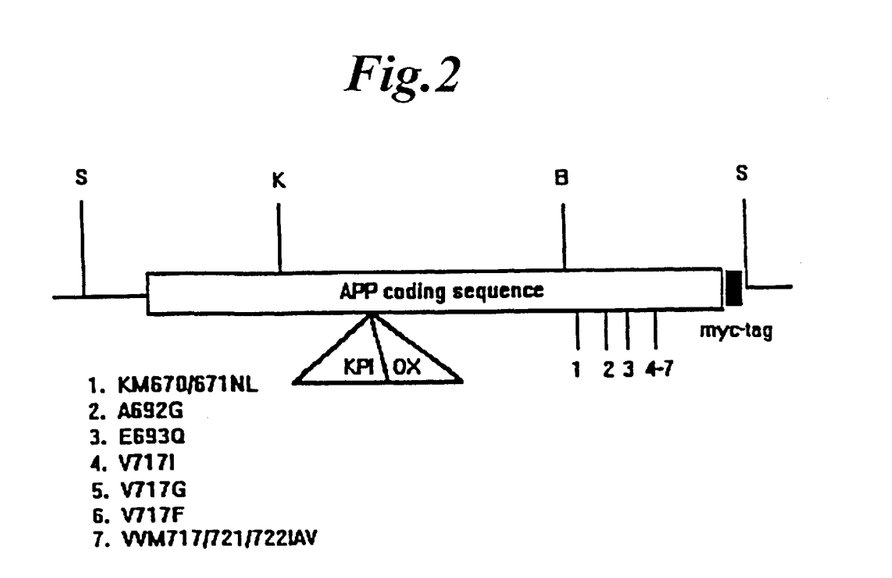
FIG. 2 is a diagrammatic representation of different APP sequences which can be expressed in transgenic animals (not exhaustive).

Gene fusions were made using the human APP protein coding sequence and the hamster prion protein gene. The human APP coding sequence derived from a human cDNA as described by Kang et al. (1987) *Nature* 325:733; Goldgabar et al. (1987); *Science* 235:877; Tanzi et al. (1987); *Science* 235:880; and Robakis et al. (1987) *P.N.A.S. U.S.A.* 84:4190 is illustrated in FIG. 1. It occurs in three splice forms which are derived from a gene located on chromosome 21 as described by Kitaguchi et al. (1988) *Nature* 331:530; Tanzi et al. (1988) *Nature* 331:528; and Ponte et al. (1988) *Nature* 331:525. FIG. 2 illustrates three features which may be incorporated into amyloid precursor protein sequences to produce the transgenic animals of the invention: (1) splice form variants which result from the presence or absence of the Kunitz protease inhibitor with or without the OX region; (2) amyloid precursor protein variants containing mutations which have been linked to illness in families with Alzheimer's disease as described by Goate et al. (1991) *Nature* 349:704; Chartier-Harlin et al. (1991) *Nature* 353:844; Murrell et al. (1991) *Science* 254:97; Hendriks et al. (1992) *Nature Genetics* 1:218; and Mullan et al. (1992) *Nature Genetics* 1:345, and families with congophilic angiopathy as described by Levy et al. (1990) *Science* 248:1124, and (3) a myc-tag at the carboxyl terminus which can be used to facilitate immunodetection of transgene products, but is preferably absent.

Figure 3:
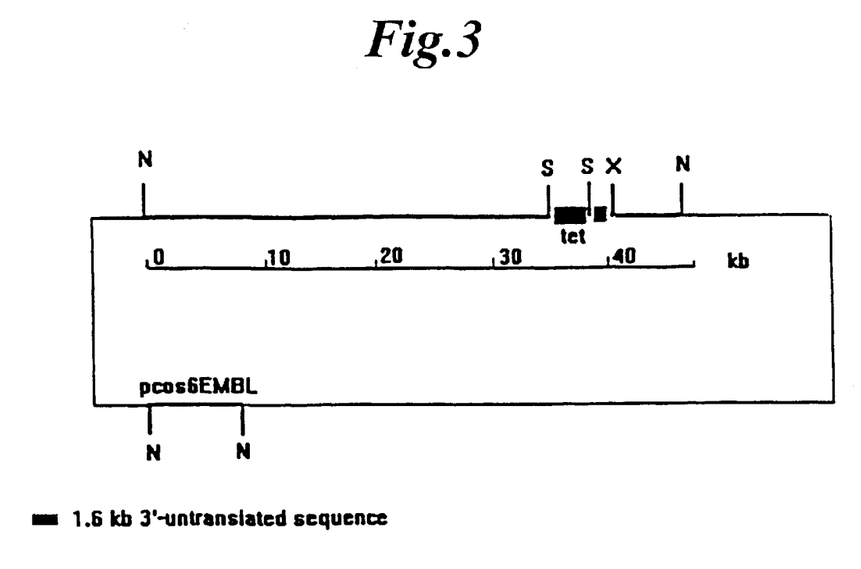
FIG. 3 is a diagrammatic representation of a hamster PrP cosmid vector with a tetracycline-resistance sequence flanked by SalI sites replacing the PrP coding sequence.

The required hamster prion protein gene functions were provided by a hamster prion protein cosmid vector in which a tetracycline-resistance sequence flanked by SalI sites replaces the prion protein coding sequence, as described by Scott et al. (1992) *Protein Science* 1:986. The hamster prion protein cosmid vector is illustrated in FIG. 3. A 1.6 KB region of DNA in the 3'-untranslated region of the prion protein gene is indicated as a useful probe for detecting transgenes made from this cosmid.

Figure 4:
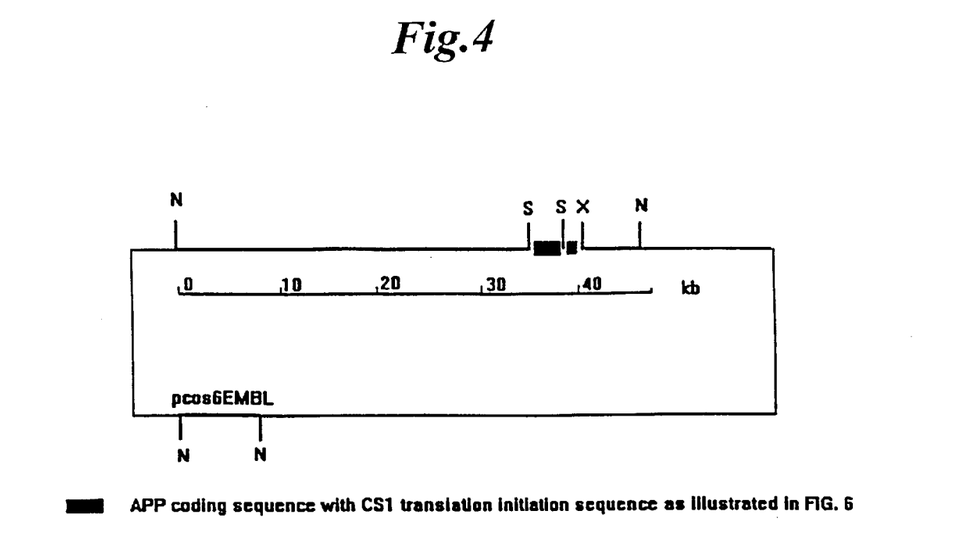
FIGS. 4 & 5 are diagrammatic representations of a hamster PrP cosmid vector fused with HuAPP sequences modified for strong translation initiation as illustrated in FIGS. 6 & 7.
Figure 5:
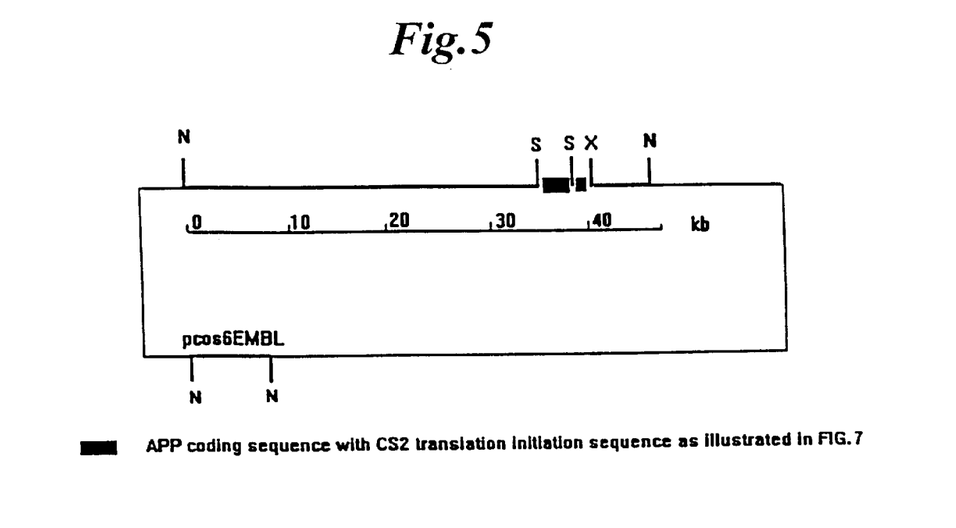

The APP sequences and cosmid were used to construct the two fusion gene constructions illustrated in FIGS. 4 and 5. The APP sequences were modified for strong translation initiation, represented by the abbreviations CS1 and CS2. The constructions were made by substituting the SalI to KpnI DNA sequence at the 5' end of the APP coding sequence for DNA sequences made using the polymerase chain reaction (PCR) and two sets of primers. For the CS1 APP sequence illustrated in FIG. 6, the primer set used was ;

5'-AAGTCGACACCATGCTGCCCGGTTTGGCACT-3' SEQ ID NO:6 and

5'-AAGGTACCTCCCAGCGCCCGAGCC-3' SEQ ID NO:7. For the CS2 APP sequence illustrated in FIG. 7, the primer set used was 5'-AAAAAAGTCGACACCATGGTGCCCGGTTTG GCACT-3' SEQ ID NO:8 and

5'-AAGGTACCTCCAGCGCCCGAGCC-3' SEQ ID NO:9.

Procedures were the conventional techniques described in Maniatis et al. (1982) Molecular Cloning: A Laboratory Manual (Cold Spring Harbor Laboratory) and the polymerase chain reaction (PCR) described in Saiki et al. (1988) *Science* 239:487. The restriction sites shown in FIGS. 1–7 are SalI (S), KpnI (K), BglII (B), XhoI (X) and NotI (N). The location of the PCR oligomers used for detecting fusion constructs in animals are indicated by A and P in FIG. 8.

Each PCR fragment synthesized for the constructions was sequenced. The PCR fragments selected for use in the constructions were free of unintended mutations.

Example 2

PRODUCTION OF TRANSGENIC MICE
CONTAINING PRP-APP FUSION GENE (APP SEQUENCE VVM717/721/722IAV)

The above PrP-APP cosmids were digested with NotI which releases the Pr.P-APP fusion gene from the poos6EMBL vector illustrated in FIGS. 3–5. The PrP-APP fusion gene was isolated after size fractionation on an agarose gel and electroeluted. The PrP-APP fusion gene was further purified in a series of organic extractions, including phenol-chloroform, chloroform, and butanol, and precipitated in ammonium acetate and ethanol. The PrP-APP fusion gene was dissolved in 10mM Tris-Cl (pH 8.0) to a final concentration of 3–4 μg/ml. Each PrP-APP fusion gene was separately injected into fertilized one-cell mouse eggs; this resulted in the integration of between 1 and 128 copies of PrP-APP fusion genes into the genomes of the mice which developed to term. The injected eggs were transferred to pseudo-pregnant foster females as described in Wagner et al. (1981) *P.N.A.S. U.S.A*. 25 78:5016. The eggs were derived from FVB matings. Mice were housed in an environmentally controlled facility maintained on a 10 hour dark: 14 hour light cycle. The eggs in the foster females were allowed to develop to term.

Example 3

ANALYSIS OF VVM717/721/722IAV TRANSGENIC MICE

At four weeks of age, each pup born was analyzed in a PCR reaction using DNA taken from the tail. In each case, tail DNA was used as a template for a PCR reaction using the probes indicated in FIG. 8.

Figure 8:
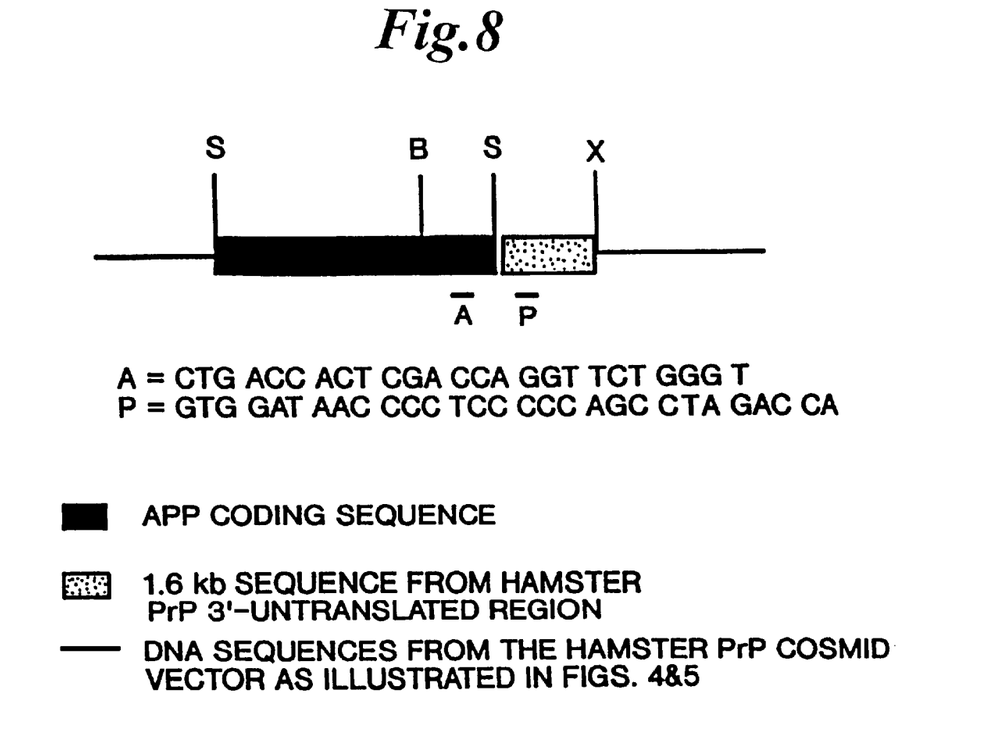
FIG. 8 is a diagrammatic representation of PCR primers which can be used to detect transgenes SEQ ID NOS:15 and 16.

The DNA for analysis was extracted from tail by the method described in Hanley and Merlie (1991) *Biotechniques* 10:56. 1 $\mu$l of the tail DNA preparation (approximately 1 $\mu$g of DNA) was used to amplify a transgene specific DNA fragment in a 25 $\mu$l PCR reaction containing primers A and P as illustrated in FIG. 8.

The PCR reactions indicated that 15 founder mice had retained an injected PrP-APP fusion gene. The APP sequence in these animals contained the VVM717/721/722IAV mutation and the myc-tag, but lacked the KPI/OX regions represented in FIG. 2. To determine transgene copy number, denatured DNA in an exponentially diluted series was probed with a 1.6 kilobase (KB) radiolabelled segment of DNA from the 3'-untranslated region of the hamster PrP gene as illustrated in FIG. 3. Among the founder mice with the highest transgene copy numbers (approximately 100 or more), two founder mice failed to breed, and a third founder sired offspring, which in turn failed to breed. Thus, the 15 founder mice yielded 12 lines of transgenic offspring. A catalog of transgenic founders with APP transgenes is shown in Table III.

acterized by progressively diminishing exploratory/locomotor behavior and premature death by five months of age. In contrast, none of nine founder animals harboring <30 copies of the PrP-APP fusion genes have developed the neurologic disease. The neurologic dysfunction was transmitted to succeeding generations in an autosomal dominant fashion.

Expression of the newly acquired PrP-APP fusion genes in tissues was determined by Western blot analysis using a monoclonal antibody, 6E10, raised to the first 17 residues of the human Aβ peptide (gift of H. Wisniewski). The fusion gene product was expressed in the brain, spinal cord, skeletal muscle, heart, and, minimally, lung. It was not detected in liver, spleen, kidney, or testis.

Expression of the PrP-APP fusion gene in brain tissue was quantitated by immunodot blot analysis. Relative APP expression was compared in transgenic and non-transgenic mice from brain tissue in an exponentially diluted series and reacted with antibody recognizing the 15 residues at the carboxyl terminus of APP, CT15, which recognizes both mouse and human APP (gift of D. Price). The total APP protein in lines of mice which developed the neurologic disease was at least 300% of endogenous levels. Where expression was less, animals did not develop neurologic disease.

To obtain an index of brain function in affected transgenic mice, glucose utilization was regionally determined using a modification of the Sokoloff method described by Chmielowska et al. (1986) *Exp. Brain Res*. 63:607, which allows glucose uptake/metabolism in the mouse to be measured. Regional 2-deoxyglucose concentrations determined densitometrically were normalized to the cerebellum, a region devoid of pathology. Results in transgenic mice revealed significant reductions in glucose utilization of 20–30% in the hippocampus, amygdala, and some regions of the cerebral cortex compared to age-matched non-transgenic littermates.

Example 4

ANALYSIS OF SYNTHESIS AND PROCESSING IN VITRO

The synthesis and processing of the VVM717/721/722IAV mutant in cultured cells was examined to determine

TABLE III

Catalogue of Transgenic Founders with APP Transgenes

| Animal ID | Transgene | Transgene Copy # | Protein Level | Status |
|---|---|---|---|---|
| Tg425L | Hacos.CS0HuAPP695-V717I.V721A.M722V | 1 | Not detectable | Sac'd |
| Tg466M | Hacos.CS0HuAPP695-WTmyc | 32-64° | 1.5–2X | Alive |
| Tg1056L | Hacos.CS1HuAPP695-V717I.V721A.M722V | 16 | | Alive |
| Tg1057H | Hacos.CS1HuAPP695-V717I.V721A.M722V | 64–128° | | Dead |
| Tg1064L | Hacos.CS1HuAPP695-V717I.V721A.M722V | 8 | | Alive |
| Tg1072L | Hacos.CS2HuAPP695-V717I.V721A.M722V | 1 | | Alive |
| Tg1073L | Hacos.CS2HuAPP695-V717I.V721A.M722V | 1 | | Alive |
| Tg1118M | Hacos.CS1HuAPP695-V717I.V721A.M722V | 32–64° | | Alive |
| Tg1119L | Hacos.CS1HuAPP695-V717I.V721A.M722V | 1 | | Alive |
| Tg1123L | Hacos.CS1HuAPP695-V717I.V721A.M722V | 1 | | Alive |
| Tg1125L | Hacos.CS1HuAPP695-V717I.V721A.M722V | 8–16 | | Alive |
| Tg1130H | Hacos.CS1HuAPP695-V717I.V721A.M722V | 64–128° | | Sick |
| Tg1135H | Hacos.CS2HuAPP695-V717I.V721A.M722V | 64–128° | | Dead |
| Tg1138H | Hacos.CS2HuAPP695-V717I.V721A.M722V | 64–128° | | Dead |
| Tg1140M | Hacos.CS2HuAPP695-V717I.V721A.M722V | 32–64° | | Alive |

The founder animals were mated to uninjected animals and the DNA of the resulting 12 lines of transgenic offspring analyzed: this analysis indicated that in every case the injected genes were transmitted through the germline.

Six founder animals harbored >30 copies of the PrP-APP fusion genes. All six developed a neurologic disease charthe consequences of these mutations. The wild-type HuAPP695myc and mutant cDNA genes were cloned into the expression vector PEF-BOSO then transiently transfected into mouse neuroblastoma cells, which were then continuously labeled with [$^{35}$S] methionine for 4 hours. Labeled APP molecules were immunoprecipitated with the monoclonal antibody 22C11. In extracts of cells, labeled APP molecules of the appropriated size were detected in similar levels (FIG. 5A). Media from these cultures was examined for the presence of soluble APP fragments using mAb 6E10 and mAb 4G8. Both of these antibodies recognize the Aβ region of human APP. The mAb 6E10 recognizes sequences in Aβ between Aβ1-17, while mAb 4G8 recognizes sequences between Aβ1-28. The sequence of Aβ17-28 is identical to mouse Aβ and thus 4G8 cannot distinguish human and mouse APP. The media of cultures transfected with either gene contained a large ectodomain fragment of APP (labeled E–F), which is routinely observed.

One of the more recent discoveries relevant to the processing of APP has been the detection of soluble Aβ1-40 fragments in the medium of cultured cells that express HuAPP. These Aβ fragments resemble peptides found in AD amyloid plaque lesions. Thus, it appears that APP is normally processed into amyloidogenic fragments. Furthermore, mutations linked to AD have been shown to alter the processing of APP to favor the production of soluble AB. To determine whether the VVM717/721/722IAV mutations affected the processing of APP, the culture medium was examined for small Aβ-containing APP peptides. An Aβ peptide fragment that was immunopurified by mAb 6E10 was prevalent in the media of cells transfected with the mutant. Similarly, the mAb 4G8 detected increased levels of Aβ peptide in the medium of cultures expressing the mutant. An examination of cell extracts for accumulated APP fragments detected increased levels of a 10 kDa APOP peptide fragment after immunoprecipitation with anti-myc polyclonal antiserum in cells expressing the mutant (FIG. 5C, line 3). Mutations generated in mutant HuAPP695myc affect the processing of APP to generate increased levels of soluble Aβ, and an intracellular C-terminal fragment of APP that is of sufficient length to include the Aβ region. Thus, the phenotype of the mutant APP created is much like that reported for human APP that encode mutations found in a Swedish kindred of AD. To date no investigators have reported increased production of Aβ as a result of expression of HuAPP that encode only the V642I AD-linked mutation (Golde et al., 1993, *Neuroscience Abstract* 19:431, 182.7). However, this mutation appears to cause a change in the length of the soluble Aβ derivative, increasing it to Aβ1-42. Thus is appears that the VVM717/721/722IAV mutations are the primary cause of the increased production of soluble Aβ. Studies on Aβ fibrillogenesis suggest that longer Aβ peptides are more amyloidogenic.

Example 5

COMPARISON OF THE PROCESSING OF HUMAN AND MOUSE APP IN MOUSE CELLS

Chimeric APP transgenes composed of mouse APP695 and human Aβ sequences were prepared and their processing evaluated. It is an hypothesis of the invention that there are differences in the way mouse and human APP are processed in mice. To construct humanized MoAPP cDNA, a MoAPP gene was cloned and mutated to make it compatible with the cosSHaPrP.535 vector. Mouse cDNA was isolated by reverse transcriptase-polymerase chain reaction (RT-PCR), and PCR primers included Xho I sites at the 5' and 3' ends for cloning purposes. To remove an internal Xho I site in the mouse cDNA, an additional primer was included that spanned the internal Xho I site (codon 397) and contained a single base substitution that eliminated the Xho I site but preserved the correct amino acid sequence. The PCR product was subsequently sequenced to verify that unwanted mutations were not created in the PCR.

The Aβ region in HuAPP and MoAPP differ by three residues, which could effect the amyloidogenic potential of the transgene product. To humanize the mouse Aβ region, a segment of the HUAPP gene that encompassed the Aβ region was amplified by PCR using primers that include a sense primer that encompassed the BglII site at codon 590 of HuAPP-695 and an antisense primer that contained two point mutations creating a NarI site at codon 626 (a cognate NarI site is found in the MoAPP cDNA), while maintaining the amino acid sequence (Table 4, primers 1 and 2). This PCR product was digested with BglII and NarI and then cloned into the BglII and NarI sites of the MoAPP CDNA. The chimeric (Mo/HuAPP) cDNA was sequenced across the BglII and NarI sites to verify that this region now contained human Aβ sequences and to verify that no other unwanted mutations were generated. To verify that this recombinant cDNA could be expressed into full-length protein, DNA was cloned into a modified pEF-BOS vector (Osaka Bioscience Institute, Osaka, Japan). The pEF-EOS vector contains the promoter element, first exon, first intron, and part of the second exon of the mammalian elongation factor 2α along with an SV40 origin of replication, permitting the replication of vectors and the high expression of genes in COS-1 cells.

COS-1 cells were transfected with pEF-BOS-Mo/HuAPP-695 [101], and cell extracts were analyzed by immunoblotting. CT15 recognized a full-length Mo/HuAPP polypeptide, whereas immunostaining with monoclonal antibody 6E10 verified that the humanized mouse cDNA product did indeed encode human AB sequences.

To generate chimeric Mo/HuAPP cDNA that encodes a double mutation linked to an early-onset AD, a PCR-based approach similar to that outlined above using primers 2 and 3 (Table 4) was employed. The template for the reactions was a cloned copy of Mo/HuAPP-695. The mutated chimeric gene was sequenced across the BglII and NarI sites to verify the presence of mutations and to be certain that no unwanted mutations existed in the transgene. The mutant Mo/HuAPP cDNA was cloned into pEF-BOS and transfected into COS-1 cells to determine whether APP polypeptides were synthesized. An APP polypeptide of the predicted size reacted with both CT15 and 6E10 antibodies.

TABLE 4

PRIMERS USED IN CONSTRUCTING RECOMBINANT APP GENES

| Primer | Sense | Sequence | | Cloning Sites | Codon Mutation |
|---|---|---|---|---|---|
| 1 | + | CCGAGATCTCTGAAGTGAAGATGGATG | SEQ ID NO:10 | Bgl II | none |
| 2 | – | AAGCTTGGCGCCTTTGTTTGAACCCAC | SEQ ID NO:11 | Nar I | none |
| 3 | + | CCGAGATCTCTGAAGTGAATCTGGATGC | SEQ ID NO:12 | Bgl II | FAD(N595,L596) |

An examination of the synthesis and processing of Mo-, Hu-, and Mo/HuAPP in mouse N2a cells has surprisingly revealed discernible differences. What is evident is that a greater percentage of MoAPP is cleaved to generate a soluble ectodomain fragment that is HuAPP. The ratio of cell-associated versus soluble moAPP is approximately 1 to 5, while 3 times more of the HuAPP is cell-associated than is soluble. The percentage of Mo/HuAPP695 that is cleaved to generate soluble ecto-fragments appears to fall between that of Mo- and HuAPP as the ratio of cell-associated to soluble Mo/HuAPP approaches 1 to 1. The majority of soluble APP ecto-fragments appear to arise from a cleavage event within Aβ at the cell surface; the differences in the ratio of cell-associated APP versus soluble ecto-fragments indicate differences in the maturation of the polypeptides. Specifically, the majority of MoAPP reaches the cell surface and is cleaved by a secretase. In contrast, HUAPP may not reach the cell surface as efficiently, thus precluding secretase cleavage. The Mo/HuAPP polypeptide appears to be intermediate between Mo and HuAPP. Alternatively, it is possible that sequences within the Aβ domain influence the efficiency of secretase cleavage.

In addition to differences in the production of soluble APP ecto-fragments, differences in the level of soluble Aβ peptides were noted. All three proteins gave rise to soluble Aβ peptides that were of a size and character consistent with identification as Aβ1-40. In cells transfected with MoAPP, a fragment that is of a size and character consistent with identification as Aβ17-40 was detected. The Aβ17-40 fragment is thought to arise after membranal cleavage of APP by the putative α-secretase, which cleaves between Aβ16 and -17. Only the Hu- and MoHuAPP derived Aβ1-40 peptides were recognized by mAb6E10 as expected. While MoAPP appeared to give rise to relatively equal amounts of Aβ1-40 and Aβ17-40, HuAPP and Mo/HuAPP were preferentially cleaved to generate only Aβ1-40. These results suggest that sequences differences within the human Aβ domain influence APP proteolytic cleavage.

Example 6

TESTING FOR DRUGS THAT PREVENT ALZHEIMER'S DISEASE

The animals of the invention can be used to test materials for the ability to confer protection against the development of Alzheimer's disease. An animal is treated with the material, in parallel with an untreated control transgenic animal. A comparatively lower incidence of the specific neurologic disease resembling Alzheimer's disease. An animal is treated with the material, in parallel with an untreated control transgenic animal. A comparatively lower incidence of the specific neurologic disease resembling Alzheimer's disease in the treated animal is detected as an indication of protection. Treated and untreated animals would be analyzed for diminished exploratory/locomotor behavior, as well as diminished 2-deoxyglucose uptake/utilization and hypertrophic gliosis in the cortico-limbic structures of the brain. To determine if a treatment can prevent or delay the onset of disease, half of the transgenic mice in a litter from a line of mice known to develop neurologic illness may be randomly assigned to receive the treatment, and the other half to receive a placebo, beginning at an age prior to the earliest known onset of disease for the given line of mice. The number of litters to be used will depend upon the magnitude of the differences observed between treated and untreated mice.

Mice may be observed daily, the diagnosis facilitated by a simple test of exploratory/locomotor behavior, the corner index test, as devised by Hsiao et al. (1994) manuscript in preparation, which may be administered three times per week by individuals blinded to the experimental groups. The corner index has 80% sensitivity and 97% specificity for diagnosing transgenic mice with neurologic disease. The 20% of sick transgenic mice which escape detection by the corner index test may be diagnosed by clinical observation (lethargy) and/or premature death. Survival curves and mean ages of disease onset and death may be calculated from the data base.

Clinical results may be corroborated by performing neuropathologic and glucose-uptake studies in samples in the experimental and control groups. Gliosis may be detected in immunohistologic studies using antibodies to glial fibrillary acidic protein. Glucose-uptake studies may be performed using a modification of the Sokoloff method described by Chmielowska et al. (1986) *Exp. Brain Res.* 63:607.

To determine if a treatment can ameliorate or cure disease, sick littermates may be randomly assigned to receive the treatment or a saline placebo. Survival and clinical improvement on the corner index test coupled with neuropathologic and glucose-uptake studies may be ascertained, as described above.

Example 7

TESTING FOR DRUGS THAT CURE ALZHEIMER'S DISEASE

The animals of the invention can be used to test materials for the ability to improve or cure Alzheimer's disease. An animal exhibiting the specific neurologic disease resembling Alzheimer's disease is treated with the material, in parallel with an untreated control transgenic animal exhibiting the neurologic disease. A comparatively delayed death, or an improvement in the neurobehavioral, pathologic, or functional indications of the disease is detected as an indication of protection. Treated and untreated animals would be analyzed for diminished exploratory/locomotor behavior, as well as diminished 2-deoxyglucose uptake/utilization and hypertrophic gliosis in the cortico-limbic structures of the brain.

As demonstrated by the above results, non-human mammals with supra endogenous levels of amyloid precursor protein show an unexpected, but striking parallel between involved regions of the neocortex in affected transgenic mice and humans with Alzheimer's disease. Glucose uptake in the sensorimotor area of the cerebral cortex was unaffected by the neurologic disease in transgenic mice. This was the only region of mouse neocortex sampled which represented mainly primary neocortex, rather than a mixture of primary and association neocortex. It is a well-known observation that in brains of patients with Alzheimer's disease, the primary neocortex is relatively free of neuropathologic findings compared to the association cortex.

Animals dying of neurologic disease exhibited hypertrophic gliosis in the hippocampus, amygdala, and some areas of the cerebral cortex. Immunohistologic mapping of HuAPP in the transgenic mice indicated widespread expression throughout the brain. However, the behavioral abnormalities corresponded to the circumscribed regions of gliotic pathology and glucose hypo-utilization found in select forebrain regions. The striking similarities in target cell specificities in cortico-limbic areas of the brain (hippocampus, amygdala, and some areas of cerebral cortex) in these transgenic mice and Alzheimer's disease support the use of these transgenic mice as a model for Alzheimer's disease.

In summary, these transgenic mice are truly unique and unprecedented in this field of research:

They express supra-endogenous levels of APP. In the lines which develop neurologic disease, APP transgene product expression with at least 200% of endogenous levels have been attained, or more than double that reported in any prior results.

More importantly, these mice have a definite, progressive neurologic disorder. Even where APP expression has been achieved in other transgenic mice, there has never been a progressive disease affecting the cortico-limbic areas of the brain.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A transgenic mouse whose genome comprises an amyloid precursor protein transgene, said transgene comprising a prion gene promoter operably linked to an amyloid precursor protein coding sequence having a mutation at amino acids 717, 721, and 722, wherein said transgenic mouse exhibits hypertrophic gliosis in the cortico-limbic region of the brain.

2. The transgenic mouse of claim 1, wherein said mouse further exhibits diminished exploratory behavior, diminished locomotor behavior, or diminished 2-deoxyglucose uptake in the cortico-limbic region of the brain.

3. The transgenic mouse of claim 1, wherein said amyloid precursor protein coding sequence encodes a human amyloid precursor protein.

4. The transgenic mouse of claim 1, wherein said mutation results in the substitution of an isoleucine, phenylalanine, or glycine residue in said amyloid precursor protein at amino acid 717.

5. The transgenic mouse of claim 1, wherein said mutation results in the, substitution of an alanine residue at amino acid 721.

6. The transgenic mouse of claim 1, wherein said mutation results in the substitution of a valine residue at amino acid 722.

7. Progeny of the mouse of claim 1, wherein said progeny exhibits hypertrophic gliosis in the cortico-limbic region of the brain.

8. A method for making a transgenic mouse exhibiting hypertrophic gliosis in the cortico-limbic region of the brain, said method comprising:

a) introducing an amyloid precursor protein transgene into an egg or an embryo of a mouse, said amyloid precursor protein transgene comprising a prion gene promoter operably linked to an amyloid precursor protein coding sequence having a mutation at amino acids 717, 721, and 722; and b) allowing said zygote comprising said amyloid precursor protein transgene to develop to term to produce said transgenic mouse.

9. The method of claim 8, wherein said mouse further exhibits diminished exploratory behavior, diminished locomotor behavior, or diminished 2-deoxyglucose uptake in the cortico-limbic region of the brain.

10. The method of claim 8, wherein said amyloid precursor protein coding sequence encodes a human amyloid precursor protein.

11. The method of claim 10, wherein said mutation results in the substitution of an isoleucine, phenylalanine, or glycine residue in amino acid 717 of said human amyloid precursor protein.

12. The method of claim 10, wherein said mutation results in the substitution of an alanine residue at amino acid 721.

13. The method of claim 10, wherein said mutation results in the substitution of a valine residue at amino acid 722.

* * * * *